(12) United States Patent
Oosawa (10) Patent No.: US 7,739,913 B2
(45) Date of Patent: Jun. 22, 2010

(54) JOINING METHOD FOR CURVED SURFACES, AND ULTRASONIC PROBE AND MANUFACTURING METHOD THEREOF

(75) Inventor: Atsushi Oosawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 385 days.

(21) Appl. No.: 11/802,144

(22) Filed: May 21, 2007

(65) Prior Publication Data

US 2007/0266792 A1    Nov. 22, 2007

(30) Foreign Application Priority Data

May 22, 2006    (JP)    ............... 2006-141516

(51) Int. Cl.
G01N 29/24    (2006.01)
H04R 31/00    (2006.01)
(52) U.S. Cl. ............... 73/649; 73/626; 73/661; 29/594
(58) Field of Classification Search ............ 73/649, 73/626, 661; 600/459, 437, 447; 29/594
See application file for complete search history.

(56) References Cited

U.S. PATENT DOCUMENTS

| | | | | |
|---|---|---|---|---|
| 3,928,901 A | * | 12/1975 | Schilling et al. | 29/889.71 |
| 3,938,372 A | * | 2/1976 | Sproule | 73/633 |
| 4,576,045 A | * | 3/1986 | Miller-Jones | 73/626 |
| 5,027,659 A | * | 7/1991 | Bele et al. | 73/626 |
| 5,235,986 A | * | 8/1993 | Maslak et al. | 600/447 |
| 5,931,684 A | * | 8/1999 | Obendorf et al. | 439/67 |
| 6,155,982 A | * | 12/2000 | Hunt | 600/459 |
| 7,530,151 B2 | * | 5/2009 | Osawa | 29/25.35 |
| 2006/0241473 A1 | * | 10/2006 | Kuniyasu | 600/459 |
| 2009/0062656 A1 | * | 3/2009 | Hyuga | 600/459 |
| 2009/0115291 A1 | * | 5/2009 | Osawa | 310/336 |

FOREIGN PATENT DOCUMENTS

| | | | |
|---|---|---|---|
| JP | 8-89505 A | | 4/1996 |
| JP | 2006253958 A | * | 9/2006 |
| JP | 2007275655 | * | 10/2007 |
| JP | 2007307288 A | * | 11/2007 |

* cited by examiner

*Primary Examiner*—J M Saint Surin
(74) *Attorney, Agent, or Firm*—Sughrue Mion, PLLC (57) ABSTRACT

A head of an ultrasonic probe is formed by joining a flexible sheet holding a plurality of ultrasonic transducers to a curved surface of a support. Concave-convex shapes (concave-convex surfaces) are provided on the curved surface of the support and a joining surface of the flexible sheet. The concave-convex surfaces correspond to each other, and are engaged with each other to determine relative positions of the flexible sheet and the support when they are joined. Each of grooves on the concave-convex surface is positioned between adjacent ultrasonic transducers.

16 Claims, 7 Drawing Sheets

JOINING METHOD FOR CURVED SURFACES, AND ULTRASONIC PROBE AND MANUFACTURING METHOD THEREOF

BACKGROUND OF THE INVENTION

1. Field of the Invention

The present invention relates to a joining method for curved surfaces in which a flexible member is joined on a curved surface of a curved member, an ultrasonic probe used for ultrasonic diagnostics, and a manufacturing method of the ultrasonic probe.

2. Description of the Related Arts

In the medical field of recent years, a medical diagnosis utilizing ultrasonic images is put to practical use. The ultrasonic image is obtained by electrically detecting echo signals, which are sent from a biologic body, with an ultrasonic observing unit connected to an ultrasonic probe via a connector. The ultrasonic observing unit applies ultrasonic waves to a relevant part of the biologic body from the ultrasonic probe. A known mode for driving the ultrasonic probe is an electronic scan mode in which a plurality of ultrasonic transducers are disposed to transmit and receive the ultrasonic waves. In this mode, the ultrasonic transducers to be driven are selectively changed by electronic switches or the like.

Regarding the ultrasonic probe of the electronic scan mode, there is a convex electronic scan mode in which the ultrasonic transducers (a number of which is 94 to 128, for example) are disposed at the top of the probe of a fan-like shape. Beside this mode, there is a radial electronic scan mode in which the ultrasonic transducers (a number of which is 360, for example) are arranged in a radial pattern at the periphery of the top of the probe.

As a method for producing such an ultrasonic probe, Japanese Patent Laid-Open Publication No. 8-089505 discloses a method in which firstly an ultrasonic transducer plate is joined on a flexible sheet (flexible member) formed of a backing material, and diced into a predetermined size, and then the flexible sheet is curved and joined along a curved surface of a convex or a cylindrical support (curved member).

However, in the method of the Japanese Patent Laid-Open Publication No. 8-089505, it is possible that relative positions of the flexible sheet and the support are misaligned (joining misalignment) in joining these two parts. Owing to this, misalignment of the ultrasonic transducers (positional misalignment) is caused, and quality of an ultrasonic image is degraded by deviation in sensitivity and frequency band of ultrasonic.

SUMMARY OF THE INVENTION

An object of the present invention is to provide a joining method for curved surfaces which can prevent the joining misalignment, and also to provide an ultrasonic probe which can prevent degradation of quality of ultrasonic images, and a manufacturing method of the ultrasonic probe.

In order to achieve the above and other objects, in a joining method for curved surfaces of the present invention, concave-convex shapes which are corresponding to each other are provided to the curved surface of the curved member and a joining surface of the flexible member. Then the concave-convex shape of the curved surface is engaged with the concave-convex shape of the joining surface, so that the flexible member is joined on the curved surface of the curved member.

It is preferable that the concave-convex shape of the curved surface and the concave-convex shape of the joining surface are not axisymmetric in each direction. In addition, it is preferable that the flexible member is a flexible sheet holding a plurality of ultrasonic transducers at an opposite surface to the joining surface.

An ultrasonic probe of the present invention comprises a support having a curved surface, a flexible sheet holding a plurality of ultrasonic transducers at an opposite surface to a joining surface which is joined on a curved surface of the support, and concave-convex shapes provided to the curved surface and the joining surface. The concave-convex shapes are corresponding to each other and engaged with each other.

It is preferable that the concave-convex shapes are formed of grooves and convex portions perpendicular to a curving direction of the flexible member, and/or forming grooves and convex portions parallel to the curving direction. In addition, it is preferable that the ultrasonic transducers are arranged along a curving direction of the flexible sheet with regular intervals, and each of the grooves or each of the convex portions on the joining surface is positioned between adjacent ultrasonic transducers.

It is preferable that the concave-convex shapes are formed such that the curved surface becomes flat at parts opposed to parts of the opposite surface on which the functional members are provided. It is preferable that the concave-convex shapes are formed by dicing. In addition, it is preferable that each of the support and the flexible sheet functions as a backing material.

According to the joining method of the present invention, since the concave-convex shapes of the curved member and the flexible member are corresponding to each other and engaged with each other to determine the relative positions of these members, the joining misalignment between the curved member and the flexible member is prevented.

In addition, since the concave-convex shape of the curved surface and the concave-convex shape of the joining surface are not axisymmetric in each direction, it is prevented that the flexible member is attached to the curved member with left-right reversal.

According to the ultrasonic probe of the present invention, since the curved surface of the support and the joining surface of the flexible sheet have the concave-convex shapes which are corresponding to each other and engaged with each other, the joining misalignment between the support and the flexible sheet is prevented. Accordingly, the positional misalignment of the ultrasonic transducers is prevented, and the degradation of quality of the ultrasonic images is prevented because of few deviations in sensitivity and frequency band of ultrasonic.

Since the ultrasonic transducers are arranged along the curving direction of the flexible sheet with regular intervals, and the concave-convex shape of the joining surface includes the grooves or convex portions each of which is positioned between adjacent ultrasonic transducers, the flexible sheet is easily curved and joined on the support. In addition, since the concave-convex shapes are formed such that the curved surface becomes flat at the parts opposed to parts of the opposite surface on which the functional members are provided, the parts of the opposite surface on each of which the ultrasonic transducer is joined are kept almost flat. Accordingly, detachment and displacement of the ultrasonic transducers due to curving of the flexible sheet are prevented, and the degradation of quality of the ultrasonic images is prevented more effectively.

In addition, since the concave-convex shape of the curved surface and the concave-convex shape of the joining surface are not axisymmetric in each direction and engaged with each other at only one relative position, it is prevented that the flexible sheet is joined to the support with left-right reversal.

BRIEF DESCRIPTION OF THE DRAWINGS

The above and other subjects and advantages of the present invention will become apparent from the following detailed description of the preferred embodiments when read in association with the accompanying drawings, which are given by way of illustration only and thus are not limiting the present invention. In the drawings, like reference numerals designate like or corresponding parts throughout the several views, and wherein:

FIGS. 7A and 7B are perspective views showing examples of variations of a concave-convex shape of the support, wherein FIG. 7A illustrates a concave-convex shape including grooves in stripe-form and a groove perpendicular to these stripe-form grooves, and wherein FIGS. 8A and 8B are perspective views showing examples of variations of the concave-convex shape of the support, wherein FIG. 8A illustrates a waffle-like concave-convex shape, and wherein

DETAILED DESCRIPTION OF THE PREFERRED EMBODIMENTS

Figure 1:
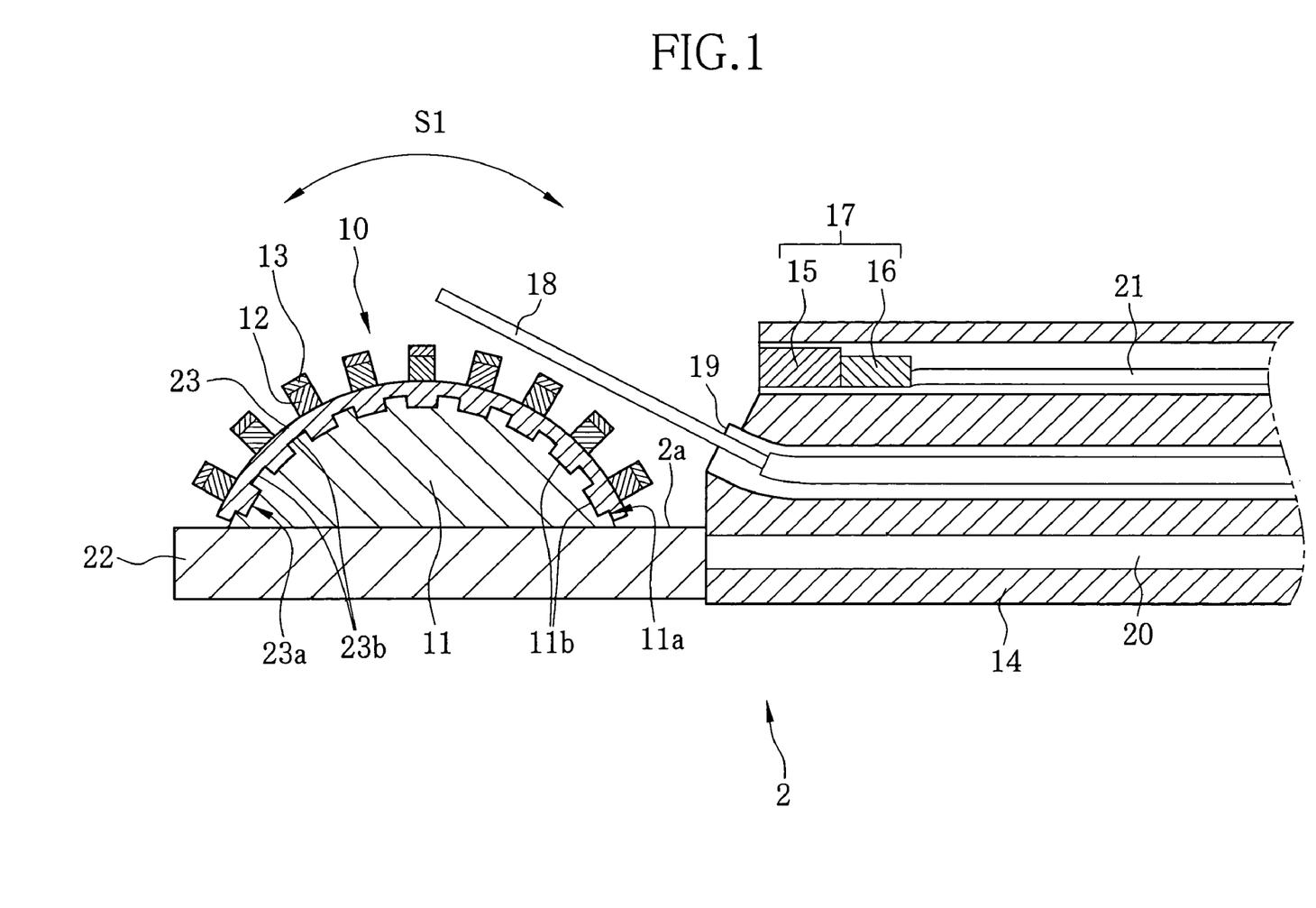
FIG. 1 is an enlarged cross-sectional diagram showing a configuration of a head of an ultrasonic probe of the present invention.
Figure 2:
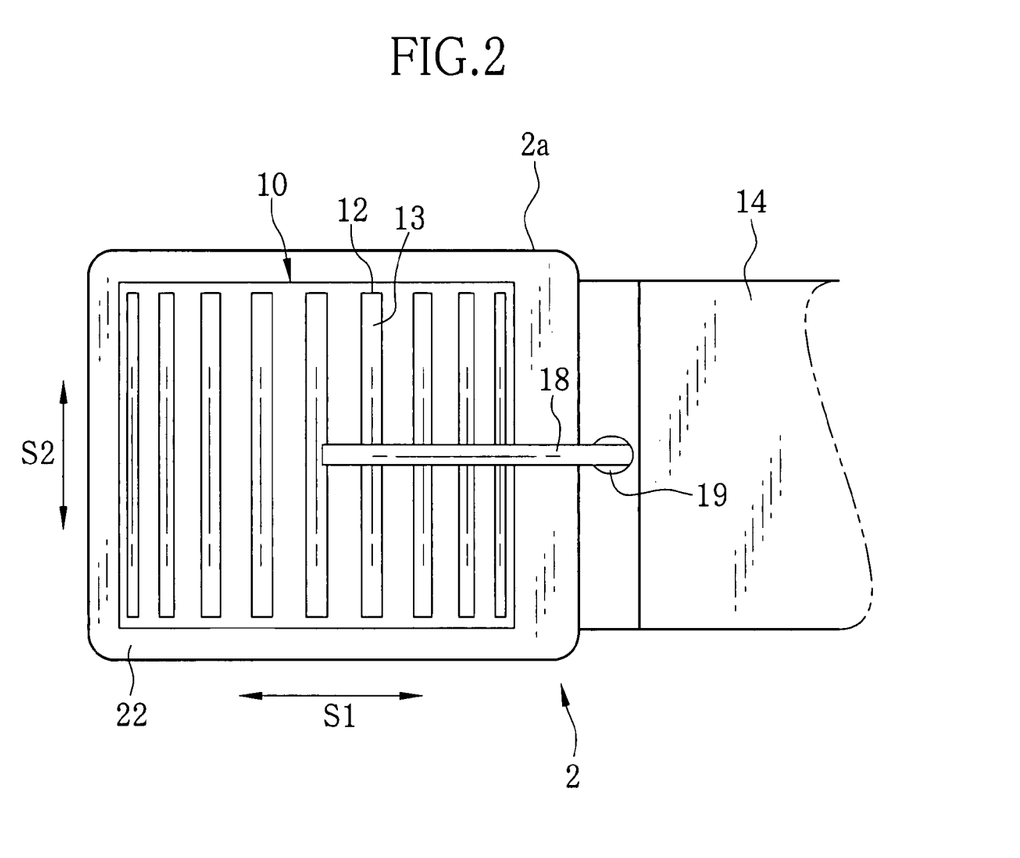
FIG. 2 is a plan view showing the configuration of the head of the ultrasonic probe.

As shown in FIGS. 1 and 2, an ultrasonic probe 2 of a convex electronic scan mode according to the present invention is provided with an ultrasonic transducer array 10 disposed at a head 2a of the ultrasonic probe 2. In the ultrasonic transducer array 10, ultrasonic transducers 12 are arranged on a curved surface of a support 11 in a one-dimensional array form along a scan direction S1. A cross section of the support 11 along the scan direction S1 has a convex shape. The ultrasonic transducer 12 has a rectangular shape elongated in a slice direction S2, on which an acoustic matching layer 13 formed of epoxy resin or the like is attached.

An imaging device 17 is disposed at an upper portion of a sheath 14 connected to the head 2a. The imaging device 17 comprises an objective optical system 15 for receiving image light of a body part to be observed, and a CCD 16 for taking the image light to output image signals. A middle portion of the sheath 14 is provided with a channel 19 into which a puncture needle 18 is inserted. Further, wiring cables 20 and 21 are inserted into the sheath 14 so as to interpose the channel 19. The wiring cable 20 electrically connects the ultrasonic transducer array 10 to an ultrasonic observing unit (not shown), and the wiring cable 21 electrically connects the imaging device 17 to the ultrasonic observing unit.

Figure 3:
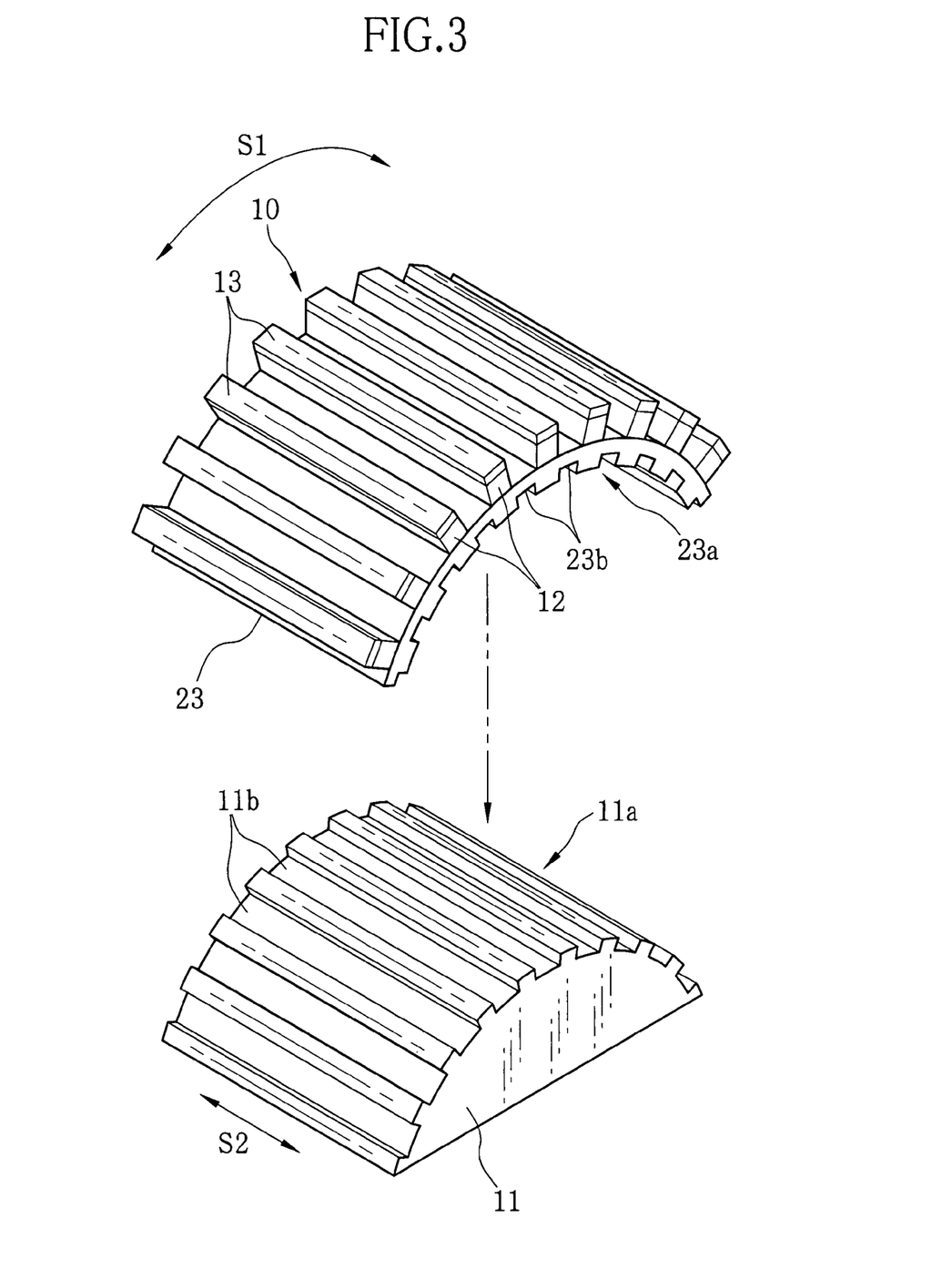
FIG. 3 is a perspective view of a support and a flexible sheet before joining.

The support 11 is placed on a base 22 of the head 2a. The support 11 is made by mixing an ultrasonic-wave attenuation material (for example ferrite powder, tungsten powder and WC2 powder) into butyl rubber or chlorinated polyethylene, and also functions as a backing material. In addition, on the curved surface of the support 11, a concave-convex surface 11a is formed. As shown in FIG. 3, the concave-convex pattern of the concave-convex surface 11a is formed by grooves 11b in stripe-form along the slice direction S2.

The ultrasonic transducer array 10 is joined to a flexible sheet 23. The flexible sheet 23 is curved along the curved surface of the support 11 and joined to the support 11. The flexible sheet 23 is formed of the same materials as the support 11, and also functions as a backing material.

On the downside of the flexible sheet 23, a concave-convex surface 23a is formed as a joining surface to the support 11. The concave-convex pattern of the concave-convex surface 23a is formed by grooves 23b in stripe-form along the slice direction S2, such that the concave-convex surface 23a and concave-convex surface 11a can be meshed (engaged) with each other. Accordingly, positioning of the support 11 and the flexible sheet 23 can be performed with high precision by the engagement between the concave-convex surfaces 11a and 23a. Note that the groove 23b is positioned not right below the ultrasonic transducer 12, but between the adjacent two ultrasonic transducers 12. A width of the groove 23b is equal to or less than a distance between the adjacent two ultrasonic transducers 12.

Although illustration is abbreviated for the purpose of avoiding complication, interspaces between the ultrasonic transducers 12 are filled with a filler of epoxy resin or the like. On the ultrasonic transducer array 10, an acoustic lens formed of silicon resin or the like is attached for converging ultrasonic radiated from the ultrasonic transducer array 10 toward a predetermined focal point.

Figure 4:
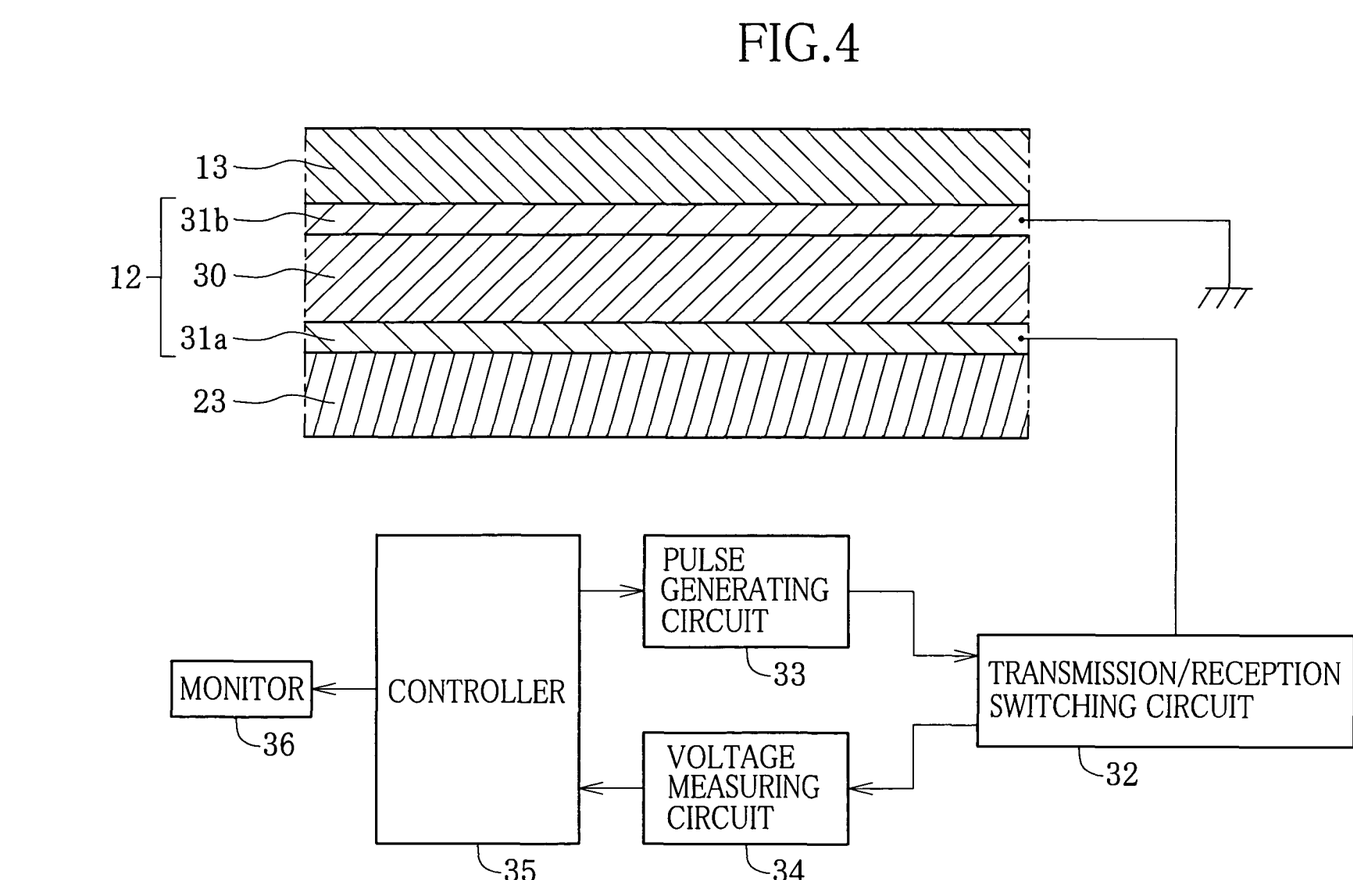
FIG. 4 is an illustration of an electrical configuration related to ultrasonic transducers.

In FIG. 4, the ultrasonic transducer 12 comprises a piezoelectric element 30 which includes a thin film of PZT (lead zirconate titanate) ceramics or the like and an individual electrode 31a and the common electrode 31b which interpose the piezoelectric element 30 between them. The individual electrode 31a is connected to a transmission/reception switching circuit 32 of the ultrasonic observing unit via a FPC (Flexible Printed Circuit, not shown), a connector and the wiring cable 20. Meanwhile, the common electrode 31b is grounded via a FPC and a connector.

The transmission/reception switching circuit 32 changes transmission and reception of the ultrasonic waves, which are performed by the ultrasonic transducer 12, at predetermined time intervals. This circuit 32 is connected to a pulse generating circuit 33 and a voltage measuring circuit 34. The pulse generating circuit 33 applies pulse voltage to the piezoelectric element 30 when the ultrasonic transducer 12 irradiates the ultrasonic waves (the time of ultrasonic wave transmission). In virtue of this, the ultrasonic transducer 12 generates the ultrasonic wave having predetermined frequency.

The voltage measuring circuit 34 measures a voltage generated by ultrasonic transducer 12 when an echo signal is received from the biologic body (the time of ultrasonic wave reception). The voltage measuring circuit 34 sends a result of this measurement to a controller 35 in which the measurement result sent from the voltage measuring circuit 34 is converted into an ultrasonic image. The converted ultrasonic image is displayed on a monitor 36.

When obtaining in vivo ultrasonic images, an insert portion of the ultrasonic probe 2 is inserted into the biologic body. While optical images obtained by the imaging device 17 are observed with an endoscopic monitor, a relevant part is searched inside the biologic body. After the head 2a has reached the relevant part, an instruction is given to obtain the ultrasonic image. Upon this instruction, a pulse voltage from the pulse generating circuit 33 is applied to the piezoelectric element 30 through the individual electrode 31a and the common electrode 31b. Accordingly, the piezoelectric element 30 is excited to irradiate ultrasonic to the relevant part.

After the irradiation of the ultrasonic, echo signals from the relevant part is received by the ultrasonic transducer 12. The irradiation of the ultrasonic and receive of the echo signals are repeated while an electronic switch such as a multiplexer (not shown) switches the ultrasonic transducers 12. Accordingly, the ultrasonic scan for the relevant part is performed along the scan direction S1. Then the echo signal is received by the voltage measuring circuit 34, and the voltage output from the ultrasonic transducer 12 is measured. The measurement result of the voltage measuring circuit 34 is sent to the controller 35 and is converted into the ultrasonic image therein. The converted ultrasonic image is displayed on the monitor 36. In addition, while the optical image or the ultrasonic image is observed, the puncture needle 18 is operated, if necessary, to take the relevant part of the biologic body.

Figure 5A:
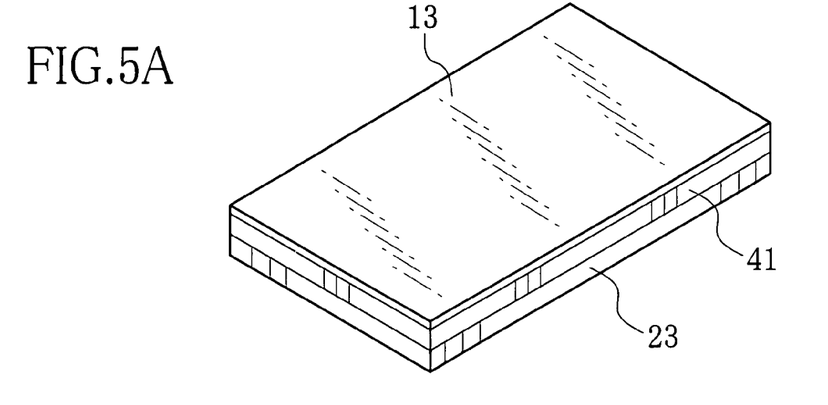
FIGS. 5A to 5C are perspective views showing processes for manufacturing an ultrasonic transducer array and a flexible sheet.

Next, manufacturing processes for the ultrasonic probe 2 having the above-described construction will be described. At first, on the flexible sheet 23, an ultrasonic transducer plate 41 having a thin plate shape is attached, as shown in FIG. 5A. On the ultrasonic transducer plate 41, the acoustic matching layer 13 is attached. Note that the ultrasonic transducer plate 41 has the construction shown in FIG. 4, that is, the piezoelectric element 30 is interposed between the individual electrode 31a and the common electrode 31b.

Figure 5B:
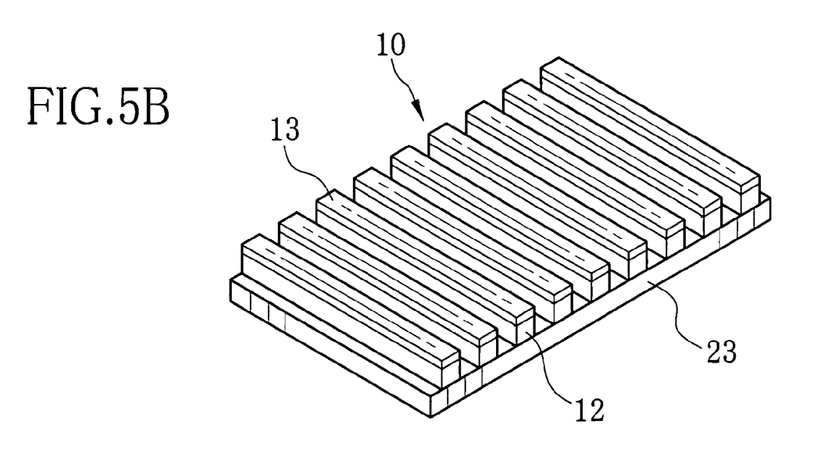

Next, as shown in FIG. 5B, the ultrasonic transducer plate 41 having the acoustic matching layer 13 thereon is diced (cut) by a dicing saw or the like, into a plurality of the ultrasonic transducers 12 each having a reed shape. A depth of dicing is controlled such that shallow slits are made on the flexible sheet 23.

Figure 5C:
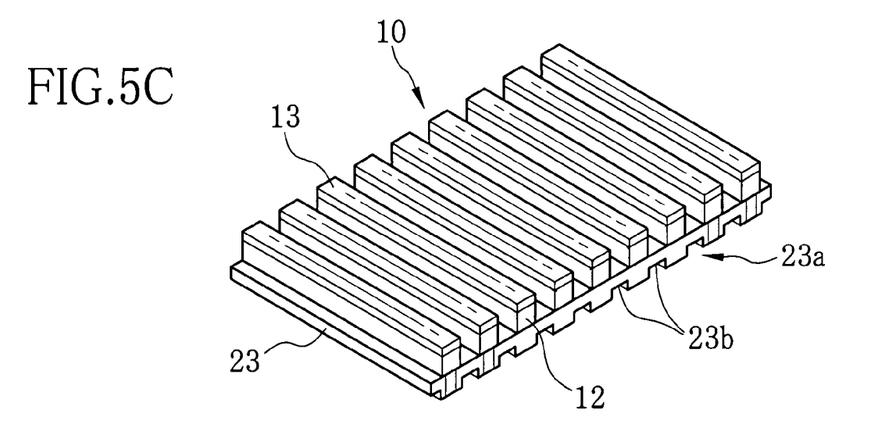

Next, as shown in FIG. 5C, the grooves 23b are formed in stripe on the down surface of the flexible sheet 23, such that each of the groove is positioned between the adjacent two ultrasonic transducers 12. Accordingly, the concave-convex surface 23a is formed. Note that the formation of the grooves 23b can be performed before the formation of the ultrasonic transducer 12.

In addition, the concave-convex surface 11a of the support 11 is formed to correspond to the shape of the concave-convex surface 23a of the flexible sheet 23. The concave-convex surface 11a is formed by injection molding or another method, with use of a mold. The concave-convex surface 11a may also be formed by dicing process.

And then as shown in FIG. 3, the flexible sheet 23 is curved along the shape of the curved surface of the support 11, and the concave-convex surface 23a of the flexible sheet 23 is fitted to the concave-convex surface 11a of the support 11 for positioning of the flexible sheet 23 and the support 11. Finally, the flexible sheet 23 is joined on the support 11 with use of a binder such as an adhesive or a primer.

After that, the filler is filled between the adjacent ultrasonic transducers 12, and the attachment of the acoustic lens and other required processes are performed. Finally, the support 11 is attached on the base 22 to finish the manufacture of the ultrasonic probe 2. Note that an explanation of an electrical wiring process for the ultrasonic transducer 12 is omitted. About the electrical wiring process, for example there is an explanation in the Japanese Patent Laid-Open Publication No. 8-089505.

As described in detail above, the concave-convex surface 11a is provided on the support 11, the concave-convex surface 23a is provided on the flexible sheet 23, and the concave-convex surface 11a and the concave-convex surface 23a are meshed with each other to determine each relative position. Accordingly, positional misalignment (displacement) of the ultrasonic transducer 12 is prevented and degradation of quality of the ultrasonic image can be prevented.

Figure 6:
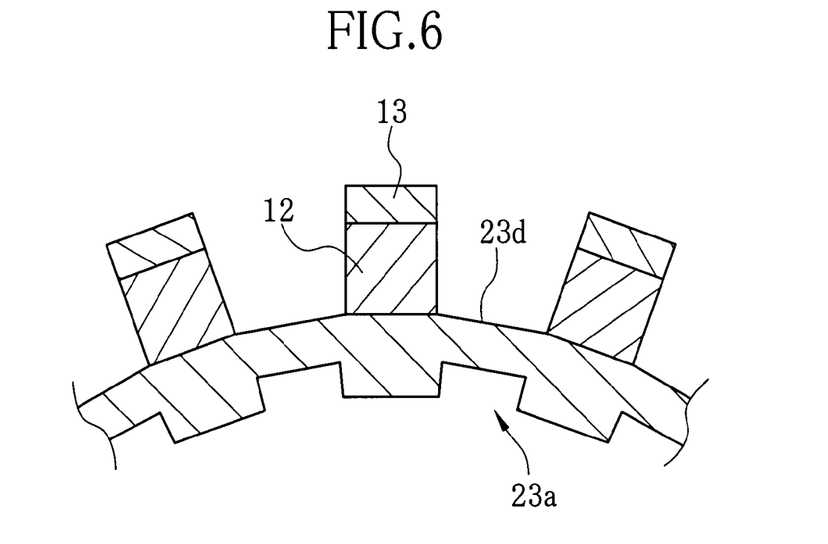
FIG. 6 is a cross-sectional diagram showing the flexible sheet curved to an approximately polygonal shape.

In addition, since the grooves 23b are formed perpendicular to the curving direction of the flexible sheet 23 (the scan direction S1), the flexible sheet 23 is easily curved and joined to the support 11. Since each groove 23b is positioned between the adjacent two ultrasonic transducers 12, the parts of the flexible sheet 23 on each of which the ultrasonic transducer 12 is joined are hardly curved (are kept almost flat). Accordingly, detachment and displacement of the ultrasonic transducers 12 due to curving of the flexible sheet 23 are prevented. As shown in FIG. 6, the concave-convex shape of the concave-convex surface 23a is preferably formed such that the curved surface of the support 11 becomes flat at the parts opposed to the parts of the outer peripheral surface 23d of the flexible sheet on which the ultrasonic transducers 12 are joined, become almost flat. In this construction, the outer peripheral surface 23d becomes a polygonal shape in microscopic view and a curved shape in macroscopic view, and each of the ultrasonic transducers 12 extends in a perpendicular direction to the flat part of the outer peripheral surface 23d. Accordingly, the detachment of the ultrasonic transducers 12 from the flexible sheet is prevented more effectively.

Figure 7A:
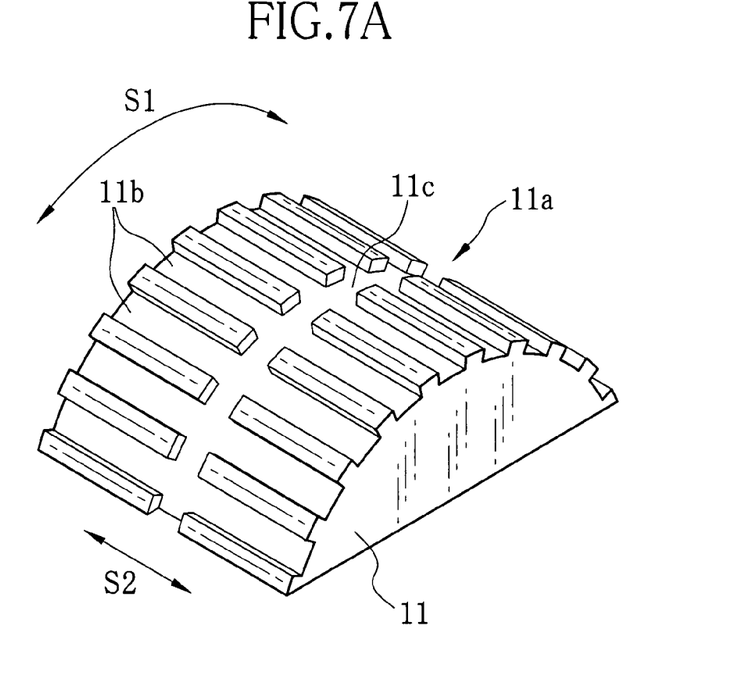

In the above embodiment, the concave-convex shapes of the concave-convex surfaces 11a and 23a are formed by the stripe-form grooves 11b and 23b. However, the concave-convex surfaces may have other shapes such as shapes shown in FIGS. 7A and 7B. In FIG. 7A, the concave-convex surface 1a is formed by a combination of the stripe-form grooves 11b parallel to the slice direction S2 and a groove 11c parallel to the scan direction S1. In this case, the relative positions of the flexible sheet 23 and the support 11 can be accurately determined not only in the scan direction S1 but also in the slice direction S2.

Figure 7B:
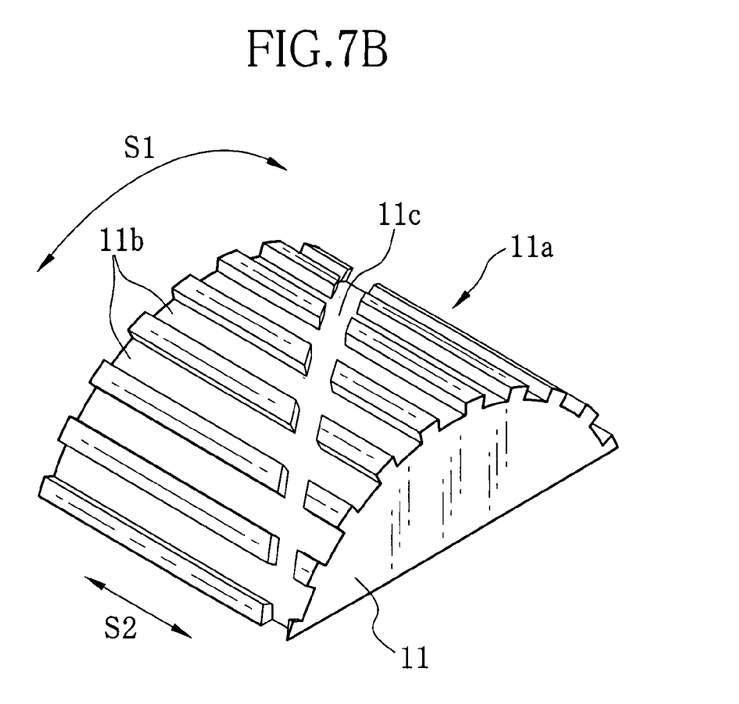
FIG. 7B illustrates a concave-convex shape including stripe-form grooves and a groove extending in an oblique direction to the stripe-form grooves.
Figure 8A:
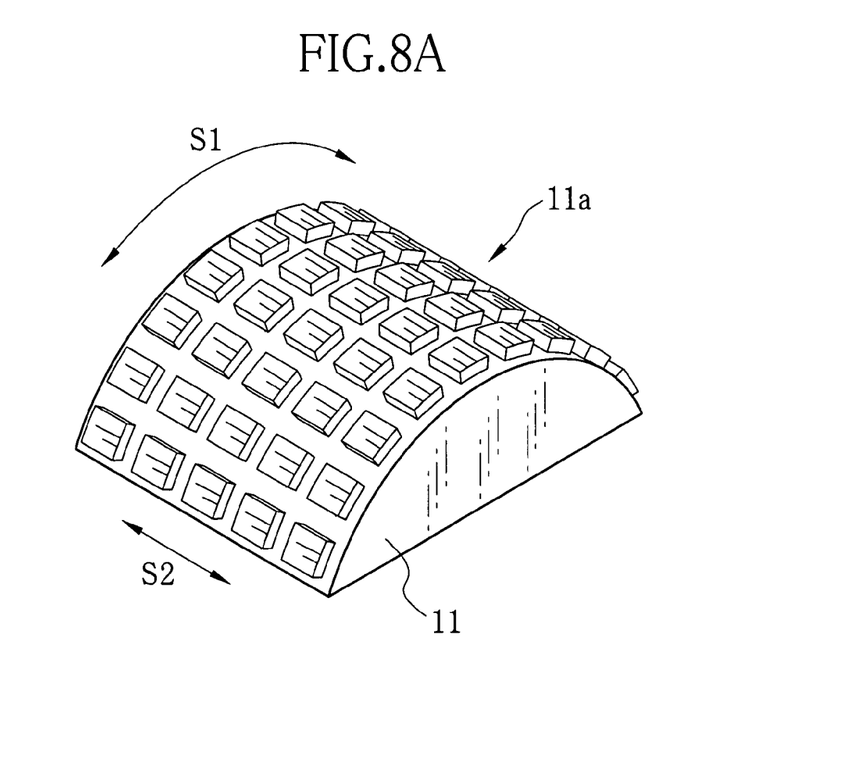
Figure 8B:
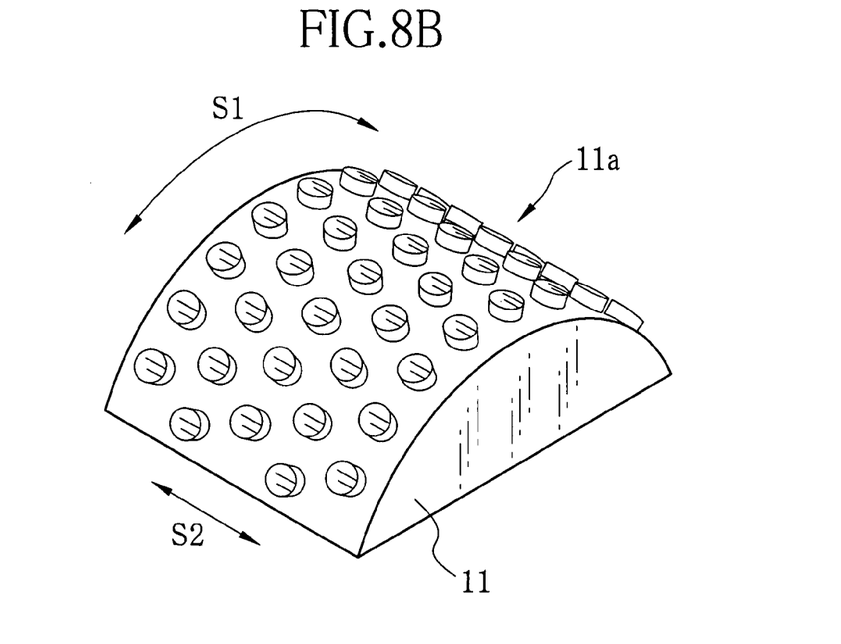
FIG. 8B illustrates a cylinders-arranged concave-convex shape.

In FIG. 7B, the groove 11c of FIG. 7A is oriented in an oblique direction. In this case, concave-convex shapes of the concave-convex surfaces 11a and 23a are not axisymmetric in each direction, and the flexible sheet 23 and the support 11 can be meshed with each other at only one relative position. That is, it is prevented that the flexible sheet 23 is attached to the support 11 with left-right reversal. In addition, as long as the concave-convex surfaces 11a and 23a can be meshed with each other, any other shapes such as a waffle-like shape shown in FIG. 8A and a cylinders-arranged shape shown in FIG. 8B may be applied for the concave-convex surfaces 11a and 23a.

In the above embodiment, the ultrasonic transducer array is the one-dimensional array where the ultrasonic transducers 12 are one-dimensionally arranged along the scan direction with regular intervals. However, the ultrasonic transducer array may be a two-dimensional array where the ultrasonic transducers 12 are two-dimensionally arranged along both the scan direction and the slice direction with regular intervals.

In the above embodiment, the ultrasonic probe of the convex electronic scan mode is used. However, the present invention can be applied also to the ultrasonic probe of the radial electronic scan mode. In this case, a support to which the flexible sheet is attached has a cylindrical shape. The ultrasonic transducers are arranged one-dimensionally or two-dimensionally on the support as same as in the convex electronic scan mode.

In the above embodiment, the support having the cylindrical shape is the curved member, and the flexible sheet holding the ultrasonic transducers is the flexible member. However, the present invention is not limited above, and there may be other combinations of the curved member and the flexible member. For example, the present invention is applicable to attachment of the acoustic lens to the ultrasonic transducer array.

In addition, since the present invention can produce the ultrasonic probe with few deviation in sensitivity and frequency band of the ultrasonic, the present invention is especially effective when applied to therapeutic ultrasonic devices for medical treatment such as heating and destruction of a relevant part, in which ultrasonic irradiated from an ultrasonic transducer array is focused at one point.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A joining method for curved surfaces, in which a flexible member is joined, on a curved surface of a curved member having a curved shape, comprising steps of:
   providing concave-convex shapes to said curved surface of said curved member and a joining surface of said flexible member, said concave-convex shapes corresponding to each other; and
   engaging said concave-convex shape of said curved surface with said concave-convex shape of said joining surface;
   wherein said concave-convex shapes are provided by forming grooves and convex portions perpendicular to a curving direction of said flexible member, and/or forming grooves and convex portions parallel to said curving direction.

2. A joining method for curved surfaces claimed in claim 1, further comprising a step of providing functional members on an opposite surface to said joining surface,
   said functional members being arranged along said curved direction with regular intervals, and
   each of said grooves or each of said convex portions on said joining surface being positioned between adjacent said functional members.

3. A joining method for curved surfaces claimed in claim 1, wherein said concave-convex shapes are formed by regularly arranging concave or convex portions having a same shape.

4. A joining method for curved surfaces claimed in claim 1, wherein said concave-convex shapes are not axisymmetric in each direction.

5. A joining method for curved surfaces claimed in claim 1, further comprising a step of providing functional members on an opposite surface to said joining surface, and
   wherein said concave-convex shapes are formed such that said curved surface becomes almost flat at parts opposed to parts of said opposite surface on which said functional members are provided.

6. A joining method for curved surfaces claimed in claim 1, wherein said concave-convex shapes are formed by dicing.

7. A joining method for curved surfaces claimed in claim 1, wherein said flexible member is a flexible sheet holding a plurality of ultrasonic transducers at an opposite surface to said joining surface.

8. An ultrasonic probe claimed in claim 7, wherein each of said support and said flexible sheet functions as a backing material.

9. An ultrasonic probe comprising:
   a support having a curved surface;
   a flexible sheet holding a plurality of ultrasonic transducers at an opposite surface to a joining surface which is joined on said curved surface of said support; and
   concave-convex shapes provided to said curved surface and said joining surface, said concave-convex shapes of said curved surface and said joining surface corresponding to each other and being engaged with each other;
   wherein said concave-convex shapes are provided by forming grooves and convex portions perpendicular to a curving direction of said flexible member, and/or forming grooves and convex portions parallel to said curving direction.

10. An ultrasonic probe claimed in claim 1 wherein said ultrasonic transducers are arranged along a curving direction of said flexible sheet with regular intervals, and each of said grooves or each of said convex portions on said joining surface is positioned between adjacent said ultrasonic transducers.

11. An ultrasonic probe claimed in claim 9, wherein said concave-convex shapes are formed by regularly arranging concave or convex portions having a same shape.

12. An ultrasonic probe claimed in claim 9, wherein said concave-convex shapes are not axisymmetric in each direction.

13. An ultrasonic probe claimed in claim 9, wherein said concave-convex shapes are formed such that said curved surface become almost flat at parts opposed to parts of said opposite surface on which said functional members we provided.

14. An ultrasonic probe claimed in claim 9, wherein said concave-convex shapes are formed by dicing.

15. A manufacturing method of an ultrasonic probe in which a flexible sheet holding a plurality of ultrasonic transducers at an opposite surface to a joining surface is joined on a curved surface of a support having a curved shape, said method comprising steps of:
   providing concave-convex shapes to said curved surface and said joining surface, said concave-convex shapes corresponding to each other; and
   engaging said concave-convex shape of said curved surface with said concave-convex shape of said joining surface;
   wherein said concave-convex shapes are provided by forming grooves and convex portions perpendicular to a curving direction of said flexible member, and/or forming grooves and convex portions parallel to said curving direction.

16. The probe of claim 9, wherein the concave shape of the curved surface includes a bottom surface, and the bottom surface is formed of material which makes up a remainder of the curved surface.

* * * * *